(12) United States Patent
Chin et al.

(10) Patent No.: US 9,456,888 B2
(45) Date of Patent: Oct. 4, 2016

(54) REVERSIBLE VASCULAR FILTER DEVICES AND METHODS FOR USING SAME

(75) Inventors: Albert K. Chin, Palo Alto, CA (US); Lishan Aklog, Scottsdale, AZ (US); Brian deGuzman, Paradise Valley, AZ (US); Michael Glennon, Norwell, MA (US)

(73) Assignee: Kaleidoscope Medical, LLC, Paradise Valley, AZ (US)

( * ) Notice: Subject to any disclaimer, the term of this patent is extended or adjusted under 35 U.S.C. 154(b) by 743 days.

(21) Appl. No.: 12/977,741

(22) Filed: Dec. 23, 2010

(65) Prior Publication Data

US 2011/0224715 A1 Sep. 15, 2011

Related U.S. Application Data

(60) Provisional application No. 61/289,508, filed on Dec. 23, 2009, provisional application No. 61/295,457, filed on Jan. 15, 2010, provisional application No. 61/304,155, filed on Feb. 12, 2010, provisional application No. 61/314,816, filed on Mar. 17, 2010.

(51) Int. Cl.
   *A61F 2/01* (2006.01)

(52) U.S. Cl.
   CPC ............ *A61F 2/01* (2013.01); *A61F 2002/016* (2013.01); *A61F 2230/005* (2013.01); *A61F 2230/008* (2013.01); *A61F 2230/0078* (2013.01)

(58) Field of Classification Search
   CPC ...... A61F 2/01; A61F 2002/016; A61F 2/90; A61F 2/86; A61F 2230/0058; A61F 2230/0078; A61F 2230/008

USPC .......................................................... 606/200
See application file for complete search history.

(56) References Cited

U.S. PATENT DOCUMENTS

| 4,425,908 A | 1/1984 | Simon |
| 4,781,177 A | 11/1988 | Lebigot |
| 5,370,657 A | 12/1994 | Irie |
| 5,725,550 A | 3/1998 | Nadal |

(Continued)

FOREIGN PATENT DOCUMENTS

| DE | 3429850 | 2/1986 |
| EP | 2 208 479 | 7/2010 |

(Continued)

OTHER PUBLICATIONS

Machine Translation of WO 9802112. Title: Extensible Filtering Sheath for Surgical Use for Vena Cava or Large Blood Vessels. Inventor: Fouere.*

(Continued)

*Primary Examiner* — Katherine Rodjom
(74) *Attorney, Agent, or Firm* — Greenberg Traurig, LLP; Chinh H. Pham

(57) ABSTRACT

The present invention provides, in one embodiment, a vascular filter device for capturing dislodged blood clots within a vessel. The vascular filter device includes an expandable framework for securing the device within a vessel. The device also includes a pathway extending through the framework. The device further includes at least one filter in alignment with the pathway for capturing dislodged clots or emboli. In an embodiment, the filter can be given form by a material that can be easily eliminated in situ to permit reestablishment of the pathway.

24 Claims, 11 Drawing Sheets

(56) References Cited

U.S. PATENT DOCUMENTS

| | | | |
|---|---|---|---|
| 6,120,534 A * | 9/2000 | Ruiz | 623/1.19 |
| 6,508,833 B2 | 1/2003 | Pavcnik et al. | |
| 7,147,649 B2 | 12/2006 | Thomas | |
| 7,261,731 B2 | 8/2007 | Patel et al. | |
| 7,722,635 B2 | 5/2010 | Beyer et al. | |
| 2001/0011187 A1 | 8/2001 | Pavcnik et al. | |
| 2003/0040772 A1* | 2/2003 | Hyodoh et al. | 606/200 |
| 2003/0139765 A1 | 7/2003 | Patel et al. | |
| 2003/0176888 A1 | 9/2003 | O'Connell | |
| 2003/0208227 A1 | 11/2003 | Thomas | |
| 2004/0059373 A1* | 3/2004 | Shapiro et al. | 606/200 |
| 2005/0171556 A1* | 8/2005 | Murphy | 606/108 |
| 2005/0288703 A1 | 12/2005 | Beyer et al. | |
| 2006/0155364 A1* | 7/2006 | Holloway et al. | 623/1.16 |
| 2008/0243170 A1* | 10/2008 | Jenson | A61B 17/221 606/200 |
| 2009/0105747 A1 | 4/2009 | Chanduszko et al. | |
| 2009/0187210 A1 | 7/2009 | Mackiewicz | |
| 2009/0198270 A1 | 8/2009 | McGuckin, Jr. et al. | |

FOREIGN PATENT DOCUMENTS

| | | | |
|---|---|---|---|
| FR | 2737654 | 2/1997 | |
| FR | WO 9802112 A1 * | 1/1998 | A61F 2/01 |
| WO | 00/66031 | 11/2000 | |
| WO | 02/22048 | 3/2002 | |
| WO | 2005/099620 | 10/2005 | |
| WO | 2006/017979 | 2/2006 | |
| WO | 2006/036457 | 4/2006 | |
| WO | 2008/010197 | 1/2008 | |
| WO | 2010/082188 | 7/2010 | |

OTHER PUBLICATIONS

International Search Report based on PCT/US10/062044 mailed Feb. 11, 2011.
International Search Report based on PCT/US10/062039 mailed Feb. 28, 2011.
International Search Report based on PCT/US10/062041 mailed Mar. 1, 2011.
Supplemental European Search Report issued in European Application No. 10840179.5 mailed May 21, 2105.

* cited by examiner

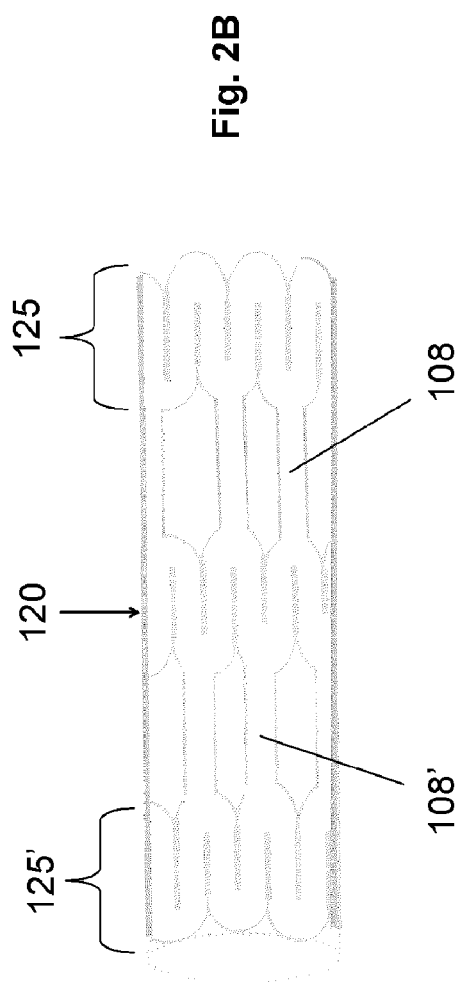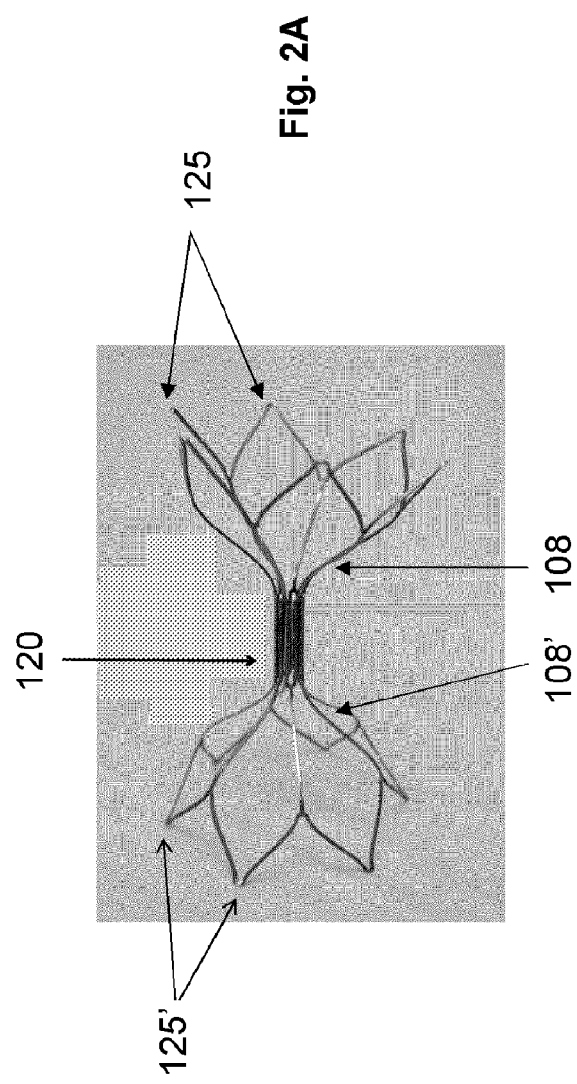

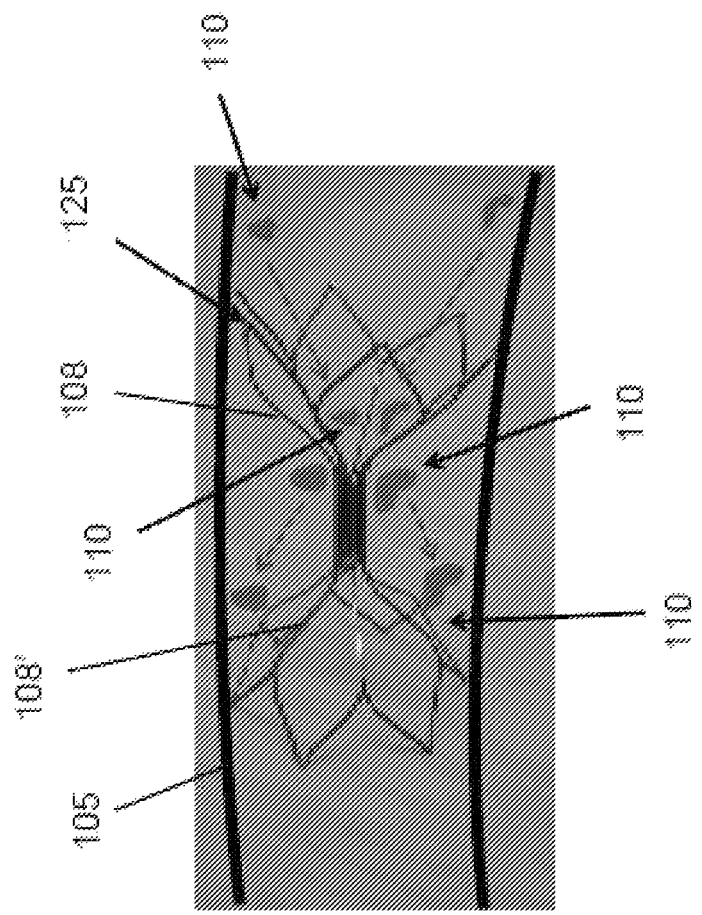

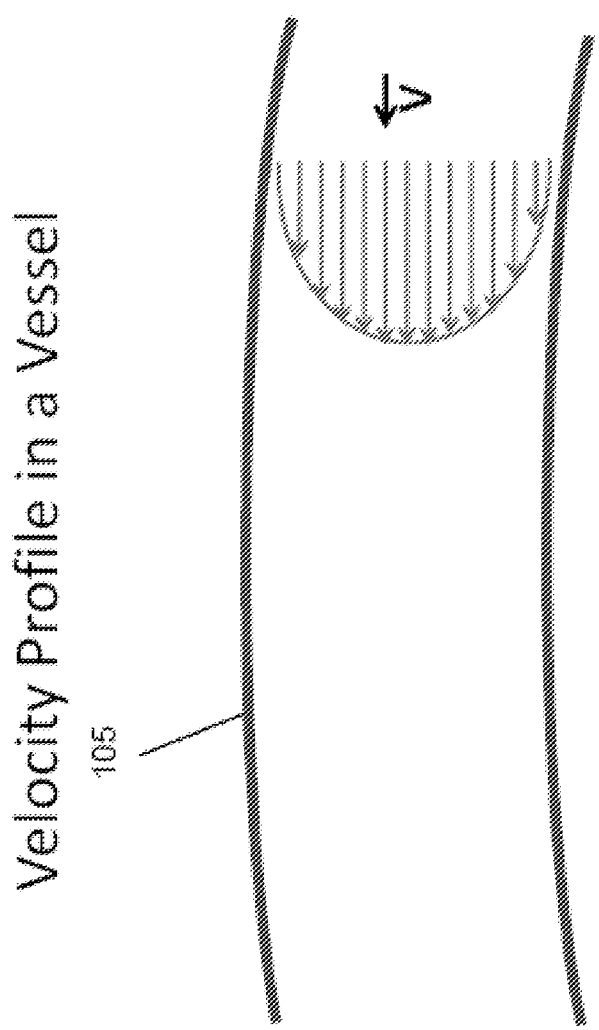

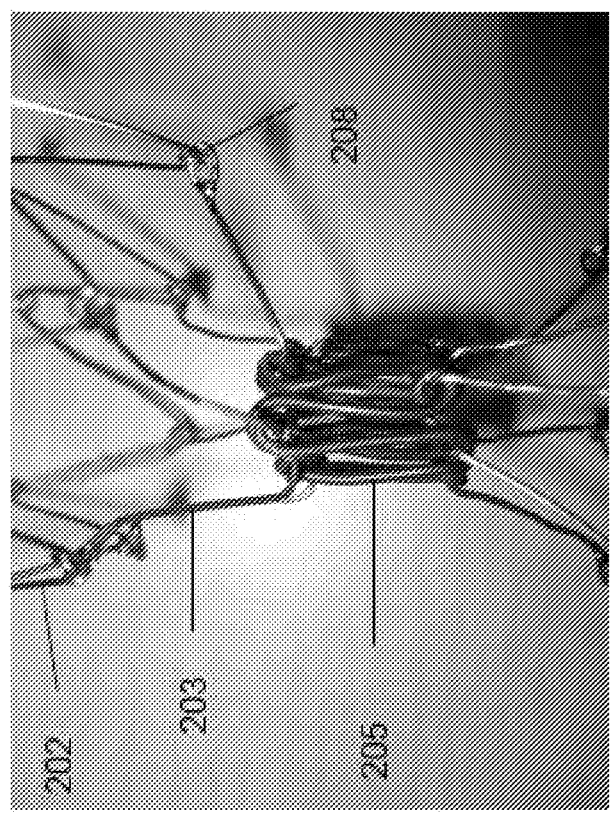

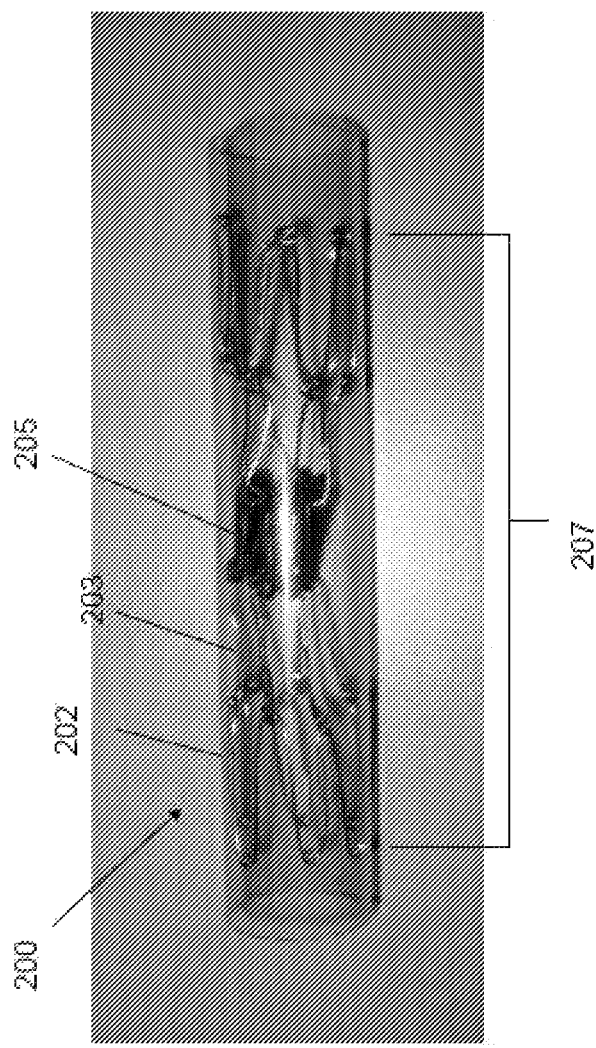

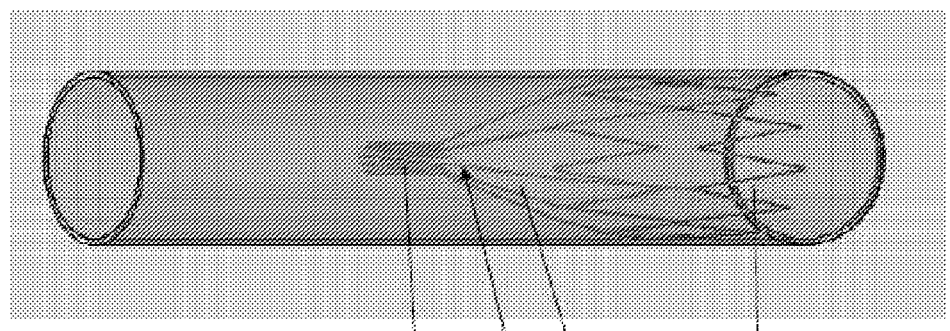
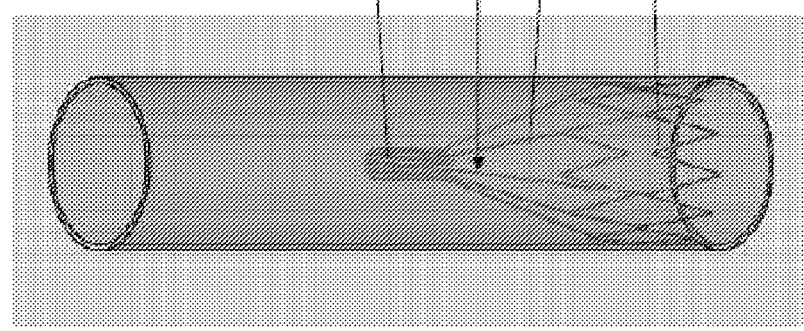
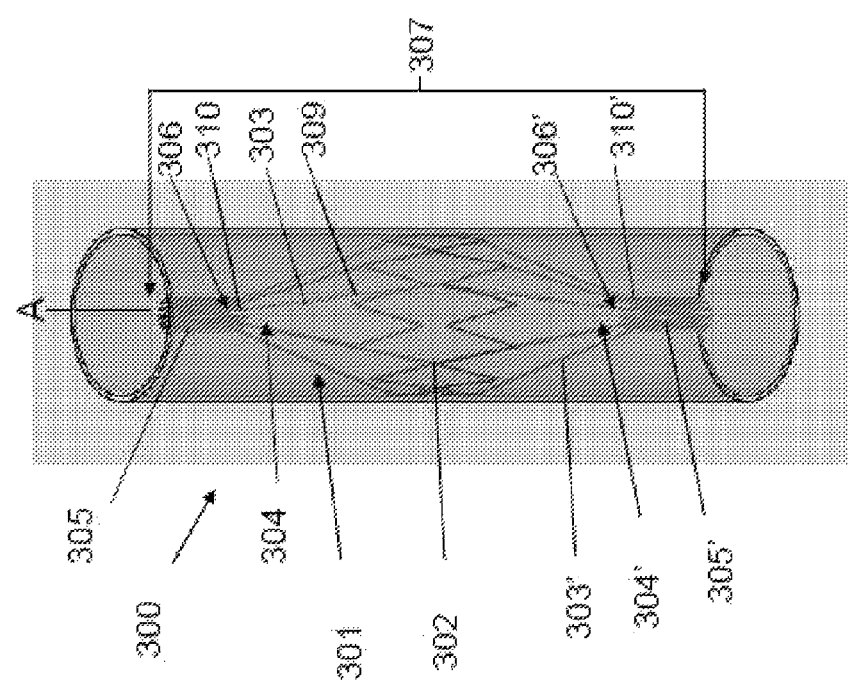

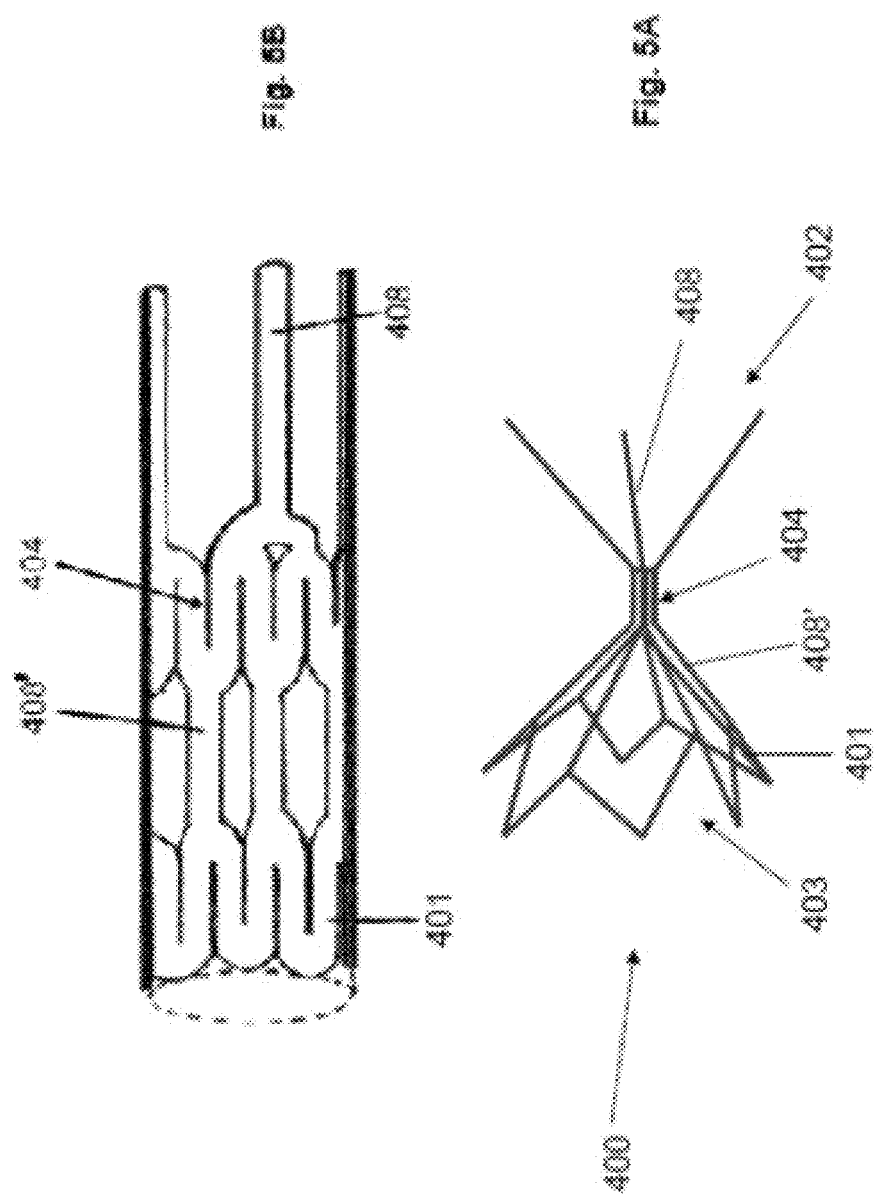

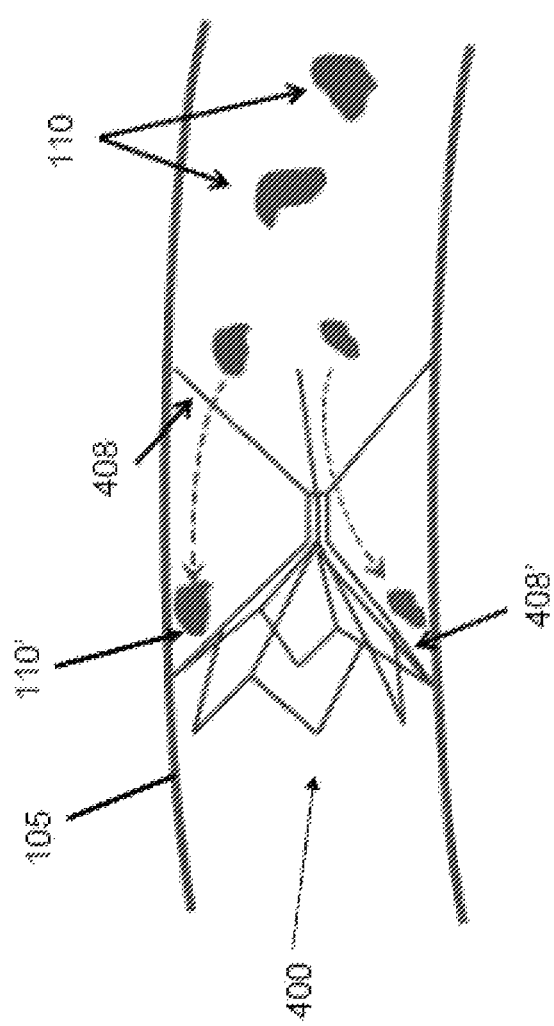

REVERSIBLE VASCULAR FILTER DEVICES AND METHODS FOR USING SAME

RELATED APPLICATIONS

The present application claims priority to and benefits of Provisional Application No. 61/289,508 filed Dec. 23, 2009, Provisional Application No. 61/295,457 filed Jan. 15, 2010, Provisional Application No. 61/304,155 filed Feb. 12, 2010, and Provisional Application No. 61/314,816 filed Mar. 17, 2010, the disclosures of all of which applications are incorporated herein by reference in their entirety.

TECHNICAL FIELD

This invention relates generally to intravascular devices and more particularly to filter devices implantable within the vena cava for capturing dislodged clots or debris.

BACKGROUND ART

Vena caval filters can be utilized in conjunction with anti-coagulants and thrombolytic agents to prevent pulmonary embolism and other vascular diseases from occurring within the body. These devices are generally implanted within a vessel, such as the inferior vena cava, to capture dislodged blood clots (emboli) contained in the blood stream. If a blood clot forms in the deep veins of a lower extremity and dislodges, the blood clot may proceed up the vena cava into the heart and into the pulmonary arteries, where it may block and interrupt blood flow. Mortality is typically high in the event of pulmonary embolism.

Filtering devices that are placed in the vena cava have been available for a number of years. Various vena caval filters have been developed over the years, including the Mobin-Uddin umbrella filter, introduced in 1967 and discontinued in 1986. The Greenfield vena caval filter has been in wide use for a number of years and is known as the standard in vena caval filters.

To trap emboli, many conventional vena caval filters employ several independent filter legs that can be expanded within the vessel to form a substantially conical-shaped filtering profile within which emboli or clots can be collected. To prevent migration of the filter within the vessel, a hook, barb or other piercing or anchoring mechanisms on the filter leg can be used to secure the filter to the wall of the vena cava. For example, the Greenfield filter has multiple legs meeting at a central apex and has attachment hooks on the legs. Deployment of the Greenfield filter often occurs in a tilted fashion, which decreases clot capture ability of the filter. Moreover, the Greenfield filter is placed in the vessel in one direction that funnels clots to the apex of the filter and the center of the vessel. In addition, the attachment hooks on the legs of the Greenfield filter are also uni-directional and positioned for funneling clot to the apex of the filter. Thus, continued use of the Greenfield filter in the vessel may lead to accumulation of clots near the apex of the filter, and may further block and interrupt blood flow near the center of the vessel.

Furthermore, it should be noted that a percentage of patients only need a vena caval filter as protection from a pulmonary embolism for a short period of time. As such, leaving an implantable filter in place for an extended period of time may lead to complications, including inferior vena cava thrombosis, deep venous thrombosis, filter migration, and vena cava perforation. Therefore, in some circumstances, it may be desirable to remove the filter from the patient.

Removal of the filter from the vena cava, however, is met with certain hurdles. For example, some of these filters may not be easily removable from a patient due to fibrous in-growth into the filter. In particular, after deployment of a filter in a patient, proliferating intimal cells can start accumulating around the filter framework in contact with the wall of the vessel. After a length of time, such accumulation or in-growth can prevent removal of the filter without risk of trauma, requiring the filter to remain in the patient.

Another hurdle to removing a filter from the vena cava results from conventional vena caval filters becoming off-centered or tilted with respect to the hub of the filter as well as the longitudinal axis of the vessel within which the filter is situated. Removal of an off-centered or tilted filter can be difficult as the barbs or hooks securing the filter in place can dig further into the vessel walls and act to injure or damage the vessel during removal.

Accordingly, it would be desirable to have an effective vena caval filter that can be eliminated after the underlying condition has passed, while avoiding damaging the tissue of the vessel wall within which the filter is located.

SUMMARY OF THE INVENTION

The present invention provides, in one embodiment, a filter device for capturing undesirable materials (e.g., clots). The device includes a first self-expanding framework for secured placement of the device against a wall of a vessel. In certain embodiments, the first self-expanding framework can include an attachment mechanism to enhance secured placement of the device against the wall of the vessel. The device further includes a malleable portion in spaced relation from the first self-expanding framework, the malleable portion designed to be dilated between a constricted diameter and a diameter substantially similar to that of the first self-expanding framework. In some embodiments, the malleable portion, upon dilation, reestablishes a pathway extending from the first self-expanding framework to the malleable portion, the pathway having substantially the same diameter therethroughout. The device also includes a plurality of arms extending from the first self-expanding framework and terminating at the malleable portion. The plurality of arms, in an embodiment, are positioned so as to capture undesirable materials flowing through the vessel and to direct the captured undesirable materials along a predefined path of the vessel, which in some embodiments is between the first self-expanding framework and the malleable portion. The plurality of arms can extend radially inward from the first self-expanding framework to the malleable portion in the neutral state. To the extent desired, the plurality of arms can be malleable.

In some examples, the filter device can further include an opposing self-expanding framework in axial alignment with the first self-expanding framework, such that the malleable portion is situated between the first self-expanding framework and the opposing self-expanding framework. In one embodiment, the device further includes a second set of plurality of arms extending from the opposing self-expanding framework and terminating at the malleable portion. The second set of plurality of arms between the opposing self-expanding framework and the malleable portion can be offset from the plurality of arms between the first self-expanding framework and the malleable portion, so as to capture undesirable materials that bypass the plurality of arms between the first self-expanding framework and the malleable portion.

In another example, the filter device further includes a second self-expanding framework adjacent to the first self-expanding framework and in axial alignment therewith. A second malleable portion in spaced relation from the second self-expanding framework can also be included and designed to be dilated between a constricted diameter and a diameter substantially similar to that of the second self-expanding framework. The device can also include a second set of plurality of arms extending from the second self-expanding framework and terminating at the second malleable portion. In an embodiment, the second set of plurality of arms between the second self-expanding framework and the second malleable portion are offset from the plurality of arms between the first self-expanding framework and the malleable portion, so as to capture undesirable materials that bypass the plurality of arms between the first self-expanding framework and the malleable portion. The second self-expanding framework and the first self-expanding framework, in one embodiment, can be separate from one another, or alternatively be integral with one another to provide substantially one framework for secured placement of the device against the wall of the vessel.

In various embodiments, the device is made of a biocompatible material.

The present invention also features methods for capturing undesirable materials using a filter device. In some embodiments, the method includes initially securing, against a wall of a vessel, a first self-expanding framework having a plurality of arms extending from the framework and radially inward to terminate at a constricted malleable portion. Next, undesirable materials may be allowed to flow into the framework toward the arms to permit the undesirable material to be captured thereat. Thereafter, the captured undesirable materials may be directed on the arms along a predefined path between the first self-expanding framework and the malleable portion. In certain embodiments, the method further includes dilating the malleable portion to establish a substantially tubular pathway extending from the first self-expanding framework to the malleable portion to minimize any interference with fluid flow through the framework.

The securing step, in one embodiment, can further include securing, against the wall of the vessel, an opposing self-expanding framework having a plurality of arms extending from the opposing framework and radially inward to terminate at the constricted malleable portion. The securing step can be so conducted such that the malleable portion is situated between the first self-expanding framework and the opposing self-expanding framework. Furthermore, to the extent desired, the securing step can include off-setting the plurality of arms between the opposing self-expanding framework and the malleable portion from the plurality of arms between the first self-expanding framework and the malleable portion. In an embodiment, undesirable materials can be permitted to pass through the set of arms between the first framework and the malleable portion and to be captured by the off-set set of arms between the opposing framework and the malleable portion. In addition, the undesirable materials captured on the off-set set of arms between the opposing framework and the malleable portion can be directed along a defined pathway on the arms away from the malleable portion.

In some embodiments, the method further includes attaching, against the wall of the vessel, a second self-expanding framework adjacent to the first self-expanding framework and in axial alignment therewith. The second framework can have a plurality of arms extending from the second framework and radially inward to terminate at a second constricted malleable portion. In an embodiment, the step of attaching includes off-setting the set of arms between the second self-expanding framework and the second malleable portion from the set of arms between the first self-expanding framework and the malleable portion. In various embodiments, undesirable materials passing through the set of arms between the first framework and the malleable portion can be captured by the off-set set of arms between the second framework and second malleable portion. To the extent desired, the second self-expanding framework and the first self-expanding framework are integral to provide substantially one framework for secured placement of the device against the wall of the vessel.

BRIEF DESCRIPTION OF DRAWINGS

FIGS. 2A-2D show another bidirectional vascular filter device in accordance with one embodiment of the present invention.

FIGS. 3A-3C show still another bidirectional vascular filter device in accordance with one embodiment of the present invention.

FIGS. 4A-4C show a uni-directional or bidirectional vascular filter device in accordance with one embodiment of the present invention.

FIGS. 5A-5C show still another uni-directional or bidirectional vascular filter device in accordance with one embodiment of the present invention.

DESCRIPTION OF SPECIFIC EMBODIMENTS

Figure 1B:
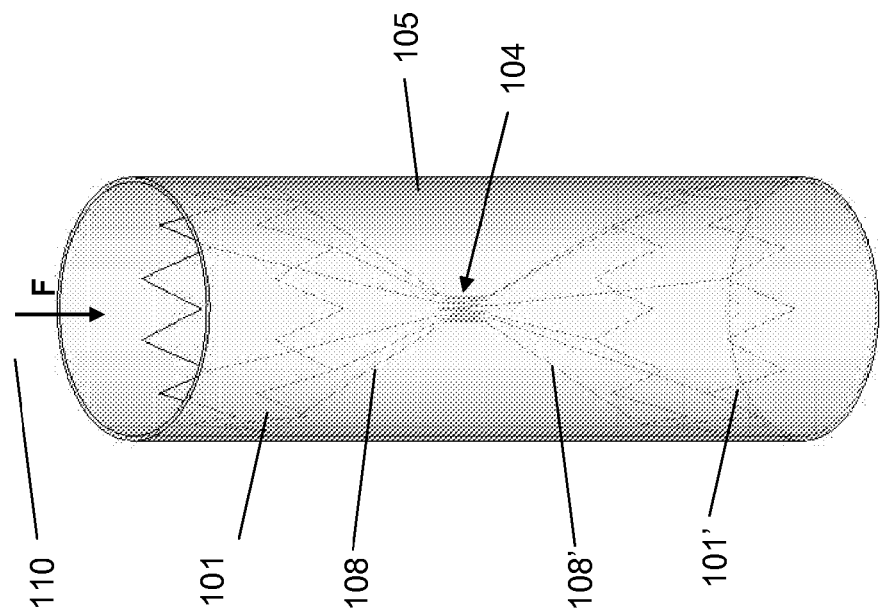
FIGS. 1A-1E show a bidirectional vascular filter device in accordance with one embodiment of the present invention.

As used herein, in addition to the other terms defined in this disclosure, the following terms may have the following meanings:

"Arms" or "legs" means an elongated member or a slender part extending from a proximal end to a distal end.

"Bidirectional" means a filter device that can be used in two opposing directions; i.e., either end can allow a fluid to flow through the filter while capturing undesirable materials. "Uni-directional" or "one-directional" means a filter device that can be used in one direction only; i.e., a fluid can flow through the filter from one end to the other only while capturing undesirable materials.

"Blood clots", "clots", "emboli" and "debris" refers to substances found within blood flow that can be filtered using the vascular filter device of the present invention. They can have various profiles (e.g., from substantially stringy to substantially globular) and sizes (e.g., from less than 1 mm to a few centimeters). "Blood clots", "clots", "emboli" and "debris" can be used interchangeably through the application. Collectively, they can be referred to as "undesirable materials."

"Collapsed" or "constricted" means that at least a portion of a filter device is in a non-expanded position. The filter device or a portion thereof would normally be in a collapsed or constricted position when introduced into a vessel and/or when retained within a cover sheath of a triaxial catheter.

"Criss-cross" pattern means a wire pattern wherein the wires cross one another.

"Device", "filter device" or "vascular filter device" means a structure for filtering in one or more vessels.

"Diameter" as used in connection with a vessel means the approximate diameter of a vessel since vessels are not often perfectly cylindrical. "Diameter" as used with respect to any structure means an approximate diameter.

"Dilated" means enlarged or expanded in width, bulk or extent.

"Expanded" means that at least a portion of a vascular filter device is in an expanded position. A vascular filter device or a portion thereof within a vessel may be expanded for the purpose of allowing fluid to substantially freely flow through the vessel. "Expanded" and "substantially expanded" may be used interchangeably when used in connection with a filtration device. "Self-expanding" means a filter device capable of expanding on its own, without external forces.

"Filter" means a device or structure having the function of holding back or capturing a material.

"Fluid" means any substance, such as a liquid or gas, that can flow, including bodily fluids, such as blood and blood plasma.

"Offset" means the relative position between two things that may otherwise be aligned but are not aligned with one another.

"Malleable" means capable of being shaped, altered or controlled by external forces or influences. "Malleable portion" means a portion of the filter device capable of switching between a constricted and an expanded position.

"Reversible" and "reversible vascular filter device" means a device that is capable of being eliminated after a period of time such that the device remains within a vessel but does not continue to filter.

"Vessel" means any vessel within a body, such as the human body, through which blood or other fluid flows and includes arteries and veins.

"Wire" means any type of wire, strand, strut or structure, regardless of cross-sectional dimension (e.g., the cross-section could be circular, oval, or rectangular) or shape, and regardless of material, that may be used to construct a filter device as described herein. Some wires may be suitable for one or more of the embodiments but not suitable for others.

In accordance with one embodiment of the present invention, systems and methods are provided herein for capturing dislodged clots or debris (e.g., emboli) within a vessel using an implantable vascular filter device. The vascular filter device of the present invention may find use in capturing dislodged clots in, for instance, the vena cava. In various embodiments, the filter device can be bi-directional such that the device may be placed in a vessel in either direction to capture clots. In this way, the need associated with uni-directional filters to place them in a particular direction (e.g., along the blood flow) can be eliminated.

Although discussed herewith in connection with the vena cava, it should be appreciated that the device of the present invention can be adapted for use within other vessels in the body. For example, a size of the vascular filter device of the present invention can be modified to the extent desired. As such, the vascular filter device of the present invention may also find use in veins and arteries, such as the abdominal aorta, aortic arch, the ascending aorta, the descending aorta, a carotid artery, an iliac artery, or a renal artery.

The vascular filter device of the present invention includes, in an embodiment, a single-piece reversible design. In other words, the reversible design of the vascular filter device of the present invention allows the device to remain within the vessel following implantation and the device, thereafter, can be deployed to not act as a filter, once such function is no longer necessary. By allowing the device to remain within the vessel following implantation, the vascular filter device of the present invention can reduce the likelihood of undesirable laceration, perforation or transection of the vessel walls associated with the removal process. The single-piece design may also ensure that the vascular filter device remains intact following implantation and can minimize detachment of components as may occur if the vascular filter device were composed of more than one piece.

Figure 1A:
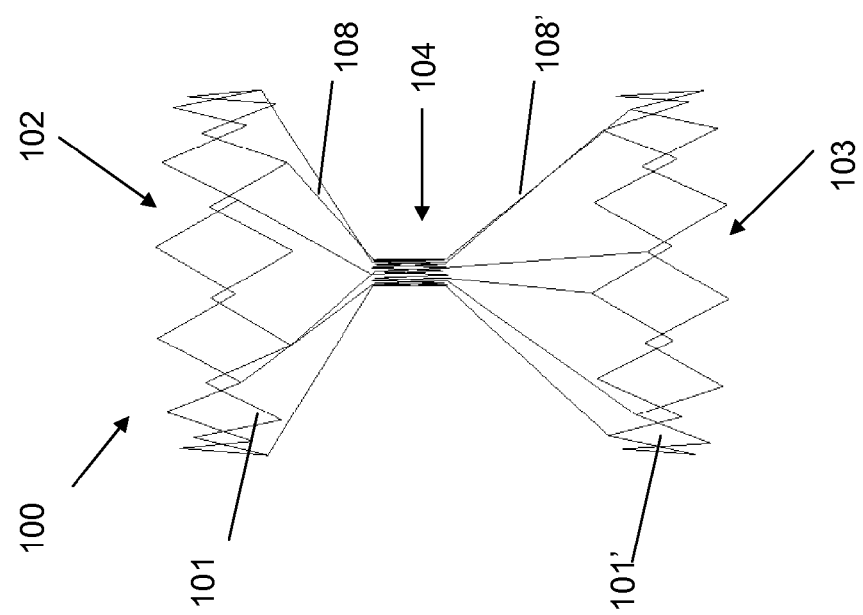

In accordance with an embodiment, FIGS. 1A-1E illustrate a design for a bidirectional vascular filter device 100 of the present invention. Vascular filter device 100, as shown in FIG. 1A, can include, in one embodiment, opposing self-expanding frameworks or bodies 101, 101' that can exert a sufficient force against a wall within a vessel 105, as shown in FIG. 1B, so as to securely position the device within the vessel 105. Frameworks 101 and 101', in one embodiment, may be made from any suitable material described below, which can be processed to have self-expanding, spring-like, or shape memory properties. In addition, should it be desired, vascular filter device 100 may be provided with barbs, hooks, or other similar attachment mechanisms on frameworks 101 and 101' to permit each framework to enhance the secured placement of the device against the wall of vessel 105.

The device 100, in an embodiment, can also have a central malleable portion 104 situated between opposing frameworks 101 and 101'. The malleable portion 104, in an embodiment, may be in a substantially collapsed or constrained position in its neutral state, and can be expanded or dilated from the substantially collapsed or constrained position to a diameter that is substantially similar to that of the frameworks 101 and 101'.

Frameworks 101 and 101' may have arms 108 and 108', respectively, connected thereto. Arms 108 and 108', in an embodiment, may extend radially inward from the frameworks 101 and 101', respectively, and terminate at malleable portion 104 to form opposing substantially conical filters 102 and 103. In an embodiment, approximately eight arms 108 and eight arms 108' may be provided about each of filters 102 and 103. Of course, the number of arms 108 and 108' can increase or decrease depending on any tradeoff between clot capture and flow rate through the frameworks 101 and 101'.

Based on its design, device 100 with the opposing self-expanding frameworks 101 and 101' can also be self-centering within a vessel. In particular, the opposing self-expanding frameworks 101 and 101' can act, by way of arms 108 and 108', to center the malleable portion 104 between the frameworks 101 and 101' upon expansion of the frameworks. In doing so, since arms 108 of filter 102 and arms 108' of filter 103 are attached the their respective framework and the now centered malleable portion 104, filter 102 and filter 103 may also be centered.

The arms 108 and 108', in an embodiment, may be positioned so as to be sufficiently spaced from one another in order to capture undesirable materials of a certain or predetermined size. In that way, each of filters 102 and 103 can capture only undesirable materials of a certain or predetermined size, and direct the captured undesirable materials substantially along a predefined path along arms 108 and 108'. The undesirable materials that may be too small to be captured by arms 108 and 108' of filters 102 and 103, respectively, may be permitted to flow through the filters, as these materials can subsequently be eliminated by the natural process of the body (e.g., being degraded and absorbed). As shown in FIG. 1B, as undesirable material 110 within a fluid flow moves along direction F into framework 101, the undesirable material 110 can be captured by at least one arm 108. In an embodiment, due to the design of arms 108, once the undesirable material is captured on an arm 108, the undesirable material can be directed along a predefined path on arm 108 toward malleable portion 104 and toward the center of the vessel 105. Although described as being captured by one arm 108, it should be appreciated that the undesirable material can extend across two or more arms 108 and be captured by multiple arms 108. In the event that the undesirable material 110 bypasses the first set of arms 108 (e.g., passing through the spaces between any two adjacent arms), the filters 102 and 103 are designed so that the bypassed material can be captured by the second set of arms 108' of filter 103 and further directed by the second set of arms 108' away from malleable portion 104 and toward the periphery of the vessel 105. To this end, the two sets of arms 108 and 108' can be offset, to the extent desired, from one another, as opposed to be in a substantially aligned relation.

In accordance with one embodiment, to permit opposing frameworks 101 and 101' to be in an expanded state and form filters 102 and 103 for capturing undesirable materials such as clots within the fluid flow, frameworks 101 and 101' may initially be treated and processed by methods known in the art to provide, for example, shape memory ability to the opposing frameworks 101 and 101', while allowing malleable portion 104 to remain in a substantially collapsed state. In an embodiment, the malleable portion 104 may stay in the substantially collapsed state by itself, without external forces. That is, when malleable portion 104 is in its neutral state, no latch, pin, hook or other physical mechanism is needed to maintain it in the collapsed state, while the filter arms 108 and 108' are in the expanded position. Furthermore, arms 108 and 108', while may be in physical contact with malleable portion 104, do not exert any substantial force to keep malleable portion 104 in the substantially collapsed state. Once shape memory ability has been imparted to the opposing frameworks 101 and 101', frameworks 101 and 101' can be collapsed and covered by a sheath to maintain the collapsed state for subsequent delivery to a site of interest. Delivery can be performed by methods known in the art, including the use of a catheter. Upon arrival at the site of interest, the sheath may be removed to allow the shaped memory end portions to expand to their natural state while pulling the arms 108 and 108' into a substantially conical configuration to form filters 102 and 103. Expansion of the end portions can also result in exertion of sufficient force, so as to securely position the frameworks 101 and 101' against the wall of the vessel 105.

Figure 1D:
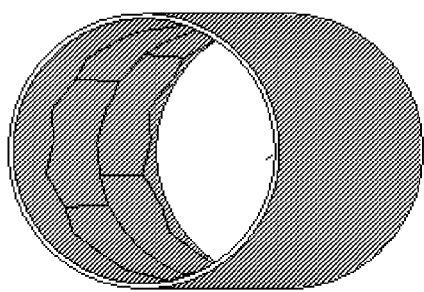
Figure 1E:
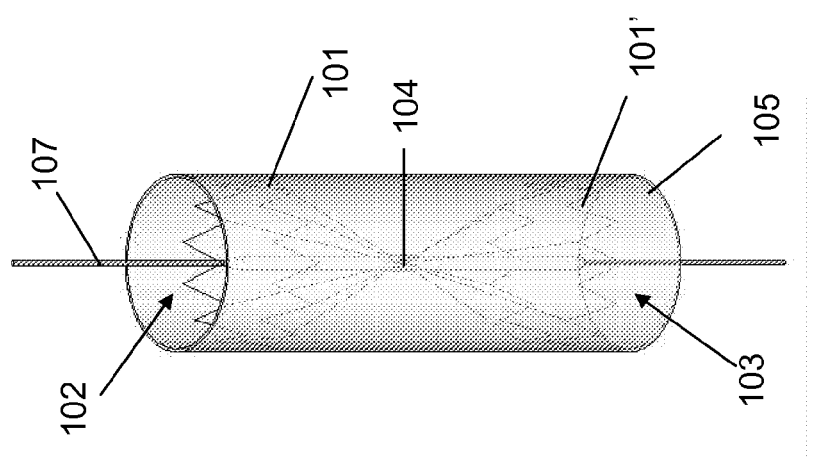
Figure 1C:
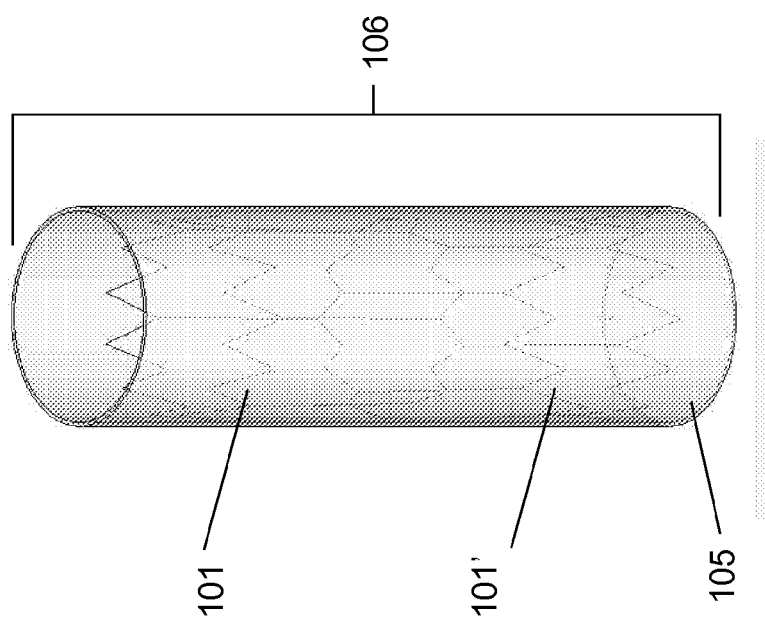

To the extent that filters 102 and 103 may no longer be needed in their active state, malleable portion 104 can be expanded, as shown in FIGS. 1C-1E, against the walls of vena cava 105 to permit pathway 106 to be established extending through the device 100 and from framework 101 to framework 101'. Looking now at FIG. 1E, to expand device 100 against wall of vessel 105, for example, a dilation balloon 107, such as an angioplasty dilation balloon, may be directed through malleable portion 104, using methods well known in the art. Thereafter, dilation balloon 107 may be inflated to expand malleable portion 104 of device 100, along with the remaining portions of device 100, including filters 102 and 103, to push the device 100 against the walls of the vessel 105 and permit establishment of pathway 106.

Filters 102 and 103, in an embodiment, may be provided with a diameter of about 40 mm at their widest part in an expanded or open position, while having an adequate radial force to retain a size of from about 20-30 mm. Of course, should it be desired, the filters can be provided with different or other diameters, depending on the application or use. In one embodiment, the arms 108 and 108' can be made from stainless steel and optionally can be processed to contain a malleable property, by known methods in the art. As for malleable portion 104, it may also be made from stainless steel wavy rings and processed to contain a malleable property, and can be expanded by a balloon. In its constricted position, the malleable portion 104 may be provided with a diameter of about 3 mm, while in the dilated position, the malleable portion 104 may be provided with a diameter substantially similar to that of the framework or to that of the filters at their widest part. The constricted diameter of the malleable portion 104, of course can be smaller or larger than 3 mm, depending on the application or use.

Since the vascular filter device 100 is designed to be implanted within a vessel of a human or animal body, the vascular filter device 100 may be made from a material that is biocompatible. The biocompatibility of the material may help minimize occurrence of adverse reactions due to implantation of the vascular filter device 100 within a vessel. In some embodiments, the vascular filter device 100 can be made entirely or partially from material that is bioresorbable, or biodegradable, or a combination thereof. In such instances, the vascular filter device 100 may be entirely or partially absorbed by the vessel or may be degraded after a certain period of time has elapsed, and would eliminate the need for manual removal of the vascular filter device 100.

In an embodiment, the material from which the framework 101 of the vascular filter device 100 may be formed includes metal, metal alloy, polymer, molded plastic, metal-polymer blend, or a combination thereof. For example, device 100 may be made from stainless steel having wavy rings similar to AAA stent graft. Device 100 may be also be a 12 sided polygon having 12 points on each end, although other geometric patterns and designs can be provided. The type of material may affect the strength and/or flexibility of the vascular filter device 100. Examples of suitable materials include stainless steel (e.g. type 304V), gold, platinum, tungsten, nitinol, nickel-titanium alloy, Beta III Titanium, cobalt-chrome alloy, cobalt-chromium-nickel-molybdenum-iron alloy, Elgiloy, L605, MP35N, Ta-10W, 17-4PH, Aeromet 100, polyethylene terapthalate (PET), polytetraflouroethylene (PTFE), polyurethane (nylon) fluorinated ethylene propylene (FEP), polyurethane, polypropylene (PP), polyvinylchloride (PVC), polyether-ester, polyester, polyamide, elastomeric polyamides, block polyamide/ethers, polyether block amide (PEBA), silicones, polyethylene, polyether-ether ketone (PEEK), polyimide (PI), polyetherimide (PEI), tantalum, tungsten, or any other suitable material that is biocompatible and that is capable of being expanded in the manner described above. Any of these materials may be subject to laser cutting to form the desired configuration (e.g., a frame) and further processed to provide shape memory ability. The vascular filter device 100 may also include an anti-thrombogenic coating such as heparin (or its derivatives), urokinase, or PPack (dextrophenylalanine proline arginine chloromethylketone) to prevent thrombosis or any other adverse reaction from occurring at the site of insertion.

FIGS. 2A-2D illustrate a design for the bidirectional vascular filter device of the present invention. The device can have a central portion 120 (e.g., malleable portion), two end portions 125 and 125' (e.g., self-expanding frameworks), and two sets of arms 108 and 108'. In an embodiment, central portion 120 can be substantially constricted or collapsed in its neutral state, and can be dilated from a constricted diameter to a diameter substantially similar to that of the end portions 125 and 125'. In this way, when the filter mode is no longer needed or desired, the constricted central portion 120 can be dilated to position the arms 108 and 108' against the vessel wall, thereby reversing the filtering function. In an embodiment, upon dilation, central portion 120 can reestablish a pathway extending between the end portions 125 and 125' with substantially the same diameter therethroughout.

In one embodiment, to make the device, a patterned frame, as shown in FIG. 2B, may be constructed or formed from a tube-like material to provide two end portions 125 and 125', and central portion 120. The tube can be made from an elastic or superelastic material. For example, a thin-walled nitinol tube can be laser cut to provide a nitinol frame. Any other materials discussed herein can also be used to construct or form the frame. In an embodiment, central portion 120 can include struts or arms 108 and 108'. End portions 125 and 125' and central portion 120, as shown in FIG. 2B, can have substantially parallel arms that are less spaced apart than arms 108 and 108' connecting the end portions 125 and 125' to central portion 120. In addition, connecting arms 108 and 108' can be so arranged that they are offset from each other.

Any of these portions can be processed to have malleable and/or self-expanding properties. For example, central portion 120 can be processed to have malleable property, as shown in FIG. 2B, and can be shaped or dilated to an expanded state therefrom. Connecting arms 108 and 108' can also be processed to have malleable property, such that when central portion 130 is being dilated, connecting arms 108 and 108', to the extent desired, can change their orientation or configuration to facilitate establishment of the pathway between the end portions 125 and 125'. End portions 125 and 125' can be processed to have self-expanding, spring property, such that they can provide secured placement of the device against the vessel wall, as shown in FIG. 2C.

When placed in a vessel, as shown in FIG. 2C, connecting arms 108 and 108' can function as filter arms by capturing and directing undesirable materials (e.g., clots) 110. Clots 110 may have various shapes, ranging from substantially linear or elongated to substantially globular. In an embodiment, as clots 110 proceeds along with the fluid flow towards the filter end 125, clots 110 may encounter the first set of filter arms 108 and be caught thereon. The first set of filter arms 108 can be arranged in a funnel shaped geometry, tending to drive the clots 110 towards the center of the filter (i.e., central portion 130) during clot capture. The second set of filter arms 108', on the other hand, can radiate out from the central portion 120 towards the wall of vessel 105. If the clots 110 are able to pass through the first set of filter arms 108 (i.e., not caught thereon), the second set of outward radiating arms 108' can act to catch clots 101. Furthermore, arms 108' can also act to drive the clots 110 towards the wall of vessel 105 (i.e., the periphery of the device, as opposed to the center of the device). It should be noted that FIG. 2C, for purposes of illustration only, shows a fluid flow direction from filter end 125 to filter end 125'. However, device 100 can also be placed in the vessel 105 in the opposite direction such that the fluid flows from filter end 125' toward filter end 125 and arms 108' and 108 act to capture undesirable materials.

Capturing clots in the periphery of the device or vessel (close to the wall of the vessel) may be clinically advantageous to the patient. The flow velocity (V) is, generally speaking, greater in the center of a vessel, compared to near the wall of the vessel. FIG. 2D shows a typical velocity profile in a vessel. By capturing clots in the periphery of the vessel, the higher velocity flow in the center of the vessel may be preserved, thereby providing less disruption to venous flow in the patient.

Furthermore, the bi-directional design with opposing filters can maintain fluid flow through the device without substantially blocking the fluid pathway within the vessel. For example, while clots 110 may accumulate on arms 108 near the center of the vessel, a fluid pathway may still be available on the periphery of the device through arms 108. Should the clots 110 bypass arms 108, the clots 110, may be captured by arms 108' and may subsequently be directed to the periphery of the device, thereby leaving a fluid pathway still available near the center of the device. As a result, a fluid pathway can be maintained even though clots 110 are caught on arms 108 and 108'.

It should be appreciated that, in addition to being self-expanding, the embodiment in FIGS. 2A-2D can also act to self-center the filters defined by arms 108 and 108'. Specifically, self-expanding end portions 125 and 125' can act by way of arms 108 and 108' to center the central portion 120 between the end portions 125 and 125' upon expansion of the end portions. In doing so, since arms 108 and arms 108' are attached the their respective end portion and the now centered central portion 120, the filters defined by arms 108 and 108' may also be centered.

Figure 3A:
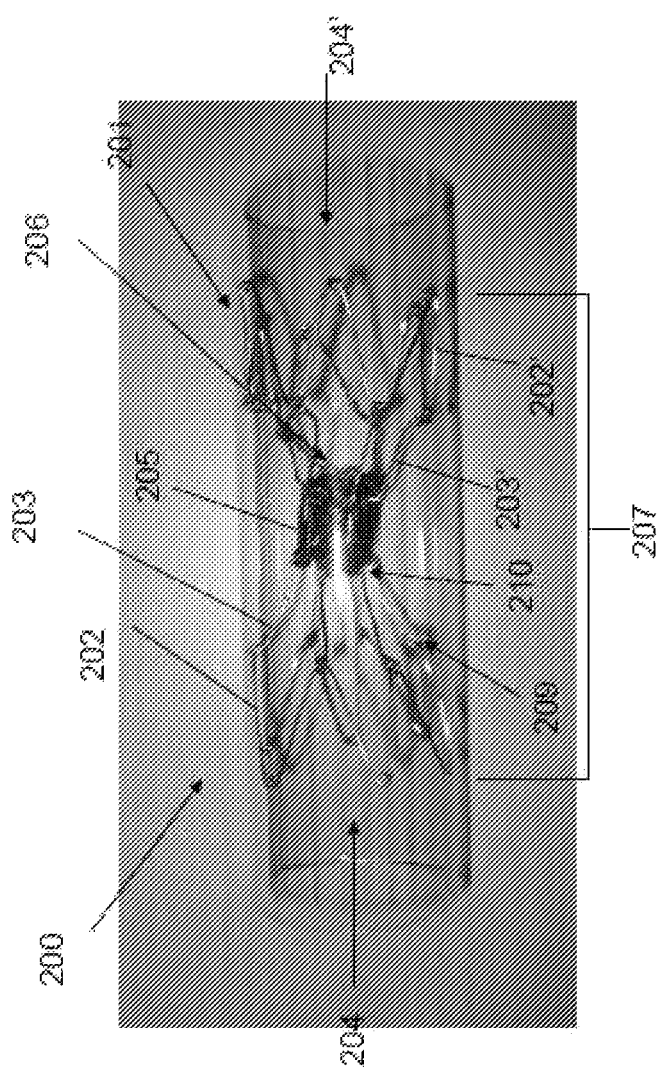

Looking now at FIGS. 3A-3C, another bidirectional vascular filter device 200 of the present invention is provided. Vascular filter device 200, as shown in FIG. 3A, includes, in one embodiment, framework 201 capable of being expanded from a collapsed state to form a bidirectional filter design within a vessel (e.g., vena cava). As with the other designs, in the expand state, the framework 201 can exert sufficient force against the wall of the vessel within which it is situated to provide the device 200 with substantial secured placement thereat. Framework 201, in one embodiment, may be made from materials similar to those noted above for the other frameworks. For example, in one embodiment, framework 201 may be made from a substantially malleable and/or self-expanding material. In addition, should it be desired, vascular filter device 200 may be provided with barbs, hooks, or other similar attachment mechanisms to permit the framework 201 to enhance secured placement of the device 200 against the wall of vessel.

In accordance with one embodiment, the framework 201 of the vascular filter device can be formed from three distinct portions. The framework 201 includes tubular portions 202 and 202' at the distal and proximal ends of framework 201 for securing the framework 201 against the vessel wall. The tubular portions 202 and 202', in an embodiment, can be made from shape memory material having self-expanding characteristics that would allow the tubular portions 202 and 202' to expand when placed into a vessel so as to secure the device 200 against the wall of the vessel. Of course, the tubular portions 202 and 202' can be made from a malleable material, if desired. In one embodiment, framework 201 may be made from a sufficiently strong material to permit the tubular portions 202 and 202' be positioned against the wall of the vessel. Examples of sufficiently strong materials include, for example, stainless steel, gold, platinum, their alloys, or any other suitable material that is sufficiently strong.

The framework 201 can further include malleable filter arms 203, having a first end 209 and a second end 210, and coupled to the tubular portion 202 at their first end 209. A second set of arms 203' can also be similarly provided such that arms 203' are coupled to tubular portion 202'. In one embodiment, the arms 203 and 203' can be positioned so that they can provide opposing filters 204 and 204' for capturing dislodged clots or debris. In their neutral state, arms 203 and 203' of opposing filters 204 and 204', respectively, can remain in a substantially conical configuration even without the aid of additional mechanisms. In an embodiment, the arms 203 of the filters 204 can approximate a frusto-conical shape, such that at their second end 210, the arms 203 do not terminate at a single point. To that end, the arms 203, at their second end 210, may together define an opening 206. Similar configuration for arms 203' can also be provided.

In an embodiment, arms 203 can be pivotally (i.e., hingedly) connected to the tubular portion 202 at their first end 209, as shown in FIGS. 3A and 3B. To allow for pivotal connection, in one embodiment, eyelets 208 may be provided at the first end 209 of the arms 203, as well as on the tubular portion 202. In that way, the arms 203 can be securely connected to the tubular portion 202. Although shown as being pivotally connected, it should be appreciated that arms 203 may be connected to the tubular portion 202 in other manners, if desired, and can also be pivotally connected without use of eyelets 208.

The framework 201, in an embodiment, can further include an unexpanded or constricted malleable portion 205 situated between the opposing filter arms 203 and 203' when the device 200 is in its neutral state. The malleable portion 205 can act, in accordance with one embodiment, to connect opposing filters 204 and 204' and to provide device 200 with a bidirectional design. When device 200 is in its neutral state, no latch, pin, hook or other physical mechanism is needed to maintain the malleable portion 205 in the collapsed state, while the filter arms 203 and 203' are in the expanded position. Moreover, when device 200 is in its neutral state, the expanded filter arms 203 and 203' of framework 201 do not act to apply any substantial force to push or hold the malleable portion 205 in the collapsed position. In an embodiment, each end of the malleable portion 205 can be pivotally (i.e., hingedly) connected to the arms 203 at the second end 210 of the arms 203, as shown in FIGS. 3A and 3B, to define opening 206 at a junction between the arms 203 and the malleable portion 205. To allow for pivotal connection, eyelets 208 may be provided at the second end 210 of the arms 203 as well as on the malleable portion 205. Although shown as being pivotally connected, it should be appreciated that malleable portion 205 may be connected to the arms 203 in other manners known in the art, if desired. Similar configuration can also be provided for arms 203' and malleable portion 205. In one embodiment, the malleable portion 205 may be made from a sufficiently strong material to permit the malleable portion 205 to connect opposing filters 204 and 204' and to provide device 200 with a bidirectional design. Examples of sufficiently strong materials include, for example, stainless steel, gold, platinum, their alloys, or any other suitable material that is sufficiently strong.

To the extent that filter arms 203 and 203' may no longer be needed in their active state, framework 201 can be expanded, as shown in FIG. 3C, against the vena cava walls to permit pathway 207 to be established through and along framework 201. To expand framework 201 against a vessel wall, a dilation balloon, such as an angioplasty dilation balloon as described above, may be directed into pathway 207 of framework 201 through malleable portion 205, using methods well known in the art. Thereafter, dilation balloon may be inflated to expand malleable portion 205 of framework 201, along with the remaining portions of framework 201, including filters 204 and 204', to push the framework 201 against the walls of the vessel and permit establishment of pathway 206 so as to allow substantially full fluid flow through device 200.

In a collapsed position, filters 204 and 204', in an embodiment, may be provided with a diameter sufficient to allow filters 204 and 204' to be fitted and/or directed within a vessel. Following expansion of the filters 204 and 204', filters 204 and 204' may be provided with a diameter sufficient for device 200 to be secured against the wall of the vessel.

It should be appreciated that although described above as being formed from a substantially malleable materials, framework 201 can, if desired, be formed entirely from shape memory material or any other material available commercially.

In accordance with one embodiment, to provide the tubular portions 202 and 202' of framework 201 with an ability to be in an expanded state and form filters 204 and 204' for capturing clots within the fluid flow, framework 201 may initially be treated and processed by methods known in the art to provide, for example, shape memory ability to the tubular portion 202 and 202' of the framework 201, while allowing the filtering arms 203 and 203' and malleable portion 205 to remain malleable and in a substantially collapsed state. By providing shape memory ability to the tubular portion 202 and 202', the tubular portion 202 and 202', when deployed within a vessel, can expand and act to pull the malleable filter arms 203 and 203' into a substantially conical configuration to form the filters 204 and 204', similar to that provided with the designs shown in FIGS. 1A-1E and FIGS. 2A-2D. Once shape memory ability has been imparted to the tubular portion 202 and 202' of framework 201, framework 201 can easily be collapsed and covered by a sheath for delivery to a site of interest. Delivery can be performed by methods known in the art, including the use of a catheter. Upon arrival at the site of interest, the sheath may be removed to allow the shaped memory tubular portions 202 and 202' to expand to their natural state to form filters 204 and 204', so as to secure the framework 201 against the wall of the vessel.

As with the previous embodiments, the device 200 illustrated FIGS. 3A-3C can be self-expanding and self-centering. In particular, the self-expanding tubular portions 202 and 202' can act by way of arms 203 and 203', respectively, to center the malleable portion 205 between the tubular portions 202 and 202'. In doing so, since arms 203 and arms 203' are attached the their respective tubular portion and the now centered malleable portion 205, filters 204 and 204' defined by arms 203 and 203', respectively, may also be centered.

In accordance with another embodiment, illustrated in FIGS. 4A-4C is another bidirectional vascular filter device 300 of the present invention. Vascular filter device 300, as shown in FIG. 4A, includes, in one embodiment, a framework 301 that is capable of being self-centered and self-expanded from a collapsed state to form a bidirectional filter design within a vessel (e.g., vena cava). Framework 301 may provide, in accordance with the present embodiment, a substantially inverted counterpart to the bidirectional filter embodiments depicted in, for example, FIGS. 1-3. While the filters 304 and 304' formed by framework 301, as described in more detail below, remain in an opposing relation, rather than facing away from one another as with the previous embodiments, filters 304 and 304' may be adjacent to each other such that the filters 304 and 304' are facing one another. Framework 301, in one embodiment, may be a single-piece design and may be made from materials similar to those noted above for the other frameworks. It should be appreciated that, if desired, framework 301 may be a multiple-piece design. In addition, should it be desired, vascular filter device 300 may be provided with barbs, hooks, or other similar attachment mechanisms to permit the framework 301 to securely position itself against the wall of vessel.

In accordance with one embodiment, the framework 301 of the vascular filter device can include three segments. In one embodiment, the framework 301 can include an expanded, tubular portion 302 (shown with a zigzag pattern in FIG. 4A; other configuration that can provide secured placement are also possible) situated in approximately the middle of framework 301 for securing the framework 301 against the vessel wall. In another embodiment, the expanded portion 302 can include two tubular portions adjacent to each other (not shown). The expanded portion 302, in an embodiment, can be made from shape memory material having self-expanding characteristics that would allow the expanded portion 302 to expand when placed into a vessel so as to secure the device 300 against the wall of the vessel. Of course, the expanded portion 302 can be made from a malleable material, if desired, such that upon implantation, expansion can be imparted by use of a balloon catheter. In one embodiment, framework 301 may be made from a sufficiently strong material to permit the expanded portion 302 be positioned against the wall of the vessel. Examples of sufficiently strong materials include, for example, stainless steel, gold, platinum, their alloys, or any other suitable material that is sufficiently strong.

The framework 301 can further include filter arms 303, having a first end 309 and a second end 310, and coupled to the expanded portion 302 at their first end 309. In one embodiment, the arms 303 can be designed to extend from the expanded portion 302 toward axis A so as to provide filter 304 with the configuration shown in FIGS. 4A-4C. Filter 304' can be provided in a similar fashion by arms 303'. In their neutral state, arms 303 and 303' of filters 304 and 304', respectively, can remain in a substantially conical configuration even without the aid of additional mechanisms. Arms 303 and 303', in an embodiment, can be so arranged that they may be offset from each other. In this way, arms 303' can act to catch materials that bypass arms 303. In an embodiment, the arms 303 and 303' of filters 304 and 304', respectively, of the filter 304 can approximate a frusto-conical shape, such that at their second end 310 and 310', respectively, the arms 303 and 303' do not terminate at a single point. To that end, the arms 303 and 303', at their second end 310 and 310', respectively, may define an opening 306 and 306', respectively. In an embodiment, the filter arms 303 and 303' can be made from a malleable material such that upon implantation, expansion can be imparted by use of a balloon catheter. Of course, if desired, filter arms 303 and 303' may be made from a self-expanding material such that expansion can occur upon implantation into a vessel.

The framework 301, in an embodiment, can further include opposing ends 305 and 305' situated at the distal and proximal ends of framework 301 in its neutral state. The opposing ends 305 and 305' can act, in accordance with one embodiment, to maintain filter arms 303 and 303', respectively, with the configuration shown in FIGS. 4A-4C. In an embodiment, the opposing ends 305 and 305' can be made from a malleable material to allow opposing ends 305 and 305' to remain unexpanded upon implantation. When device 300 is in its neutral state, no latch, pin, hook or other physical mechanism is needed to maintain the opposing ends 305 and 305' in the collapsed state, while the filter arms 303 and 303' are in the expanded position. Furthermore, filter arms 303 and 303', while may be in physical contact with opposing ends 305 and 305', do not exert any substantial force to keep them in the substantially collapsed state. In one embodiment, the opposing ends 305 and 305' may be made from a sufficiently strong malleable material to maintain filter arms 303 and 303' with the configuration shown in FIGS. 4A-4C. Examples of sufficiently strong materials include, for example, stainless steel, gold, platinum, their alloys, or any other suitable material that is sufficiently strong.

To the extent that filters 304 and 304' may no longer be needed in their active state, framework 301 can be expanded against the vena cava walls to permit pathway 307 to be established through and along framework 301. To expand framework 301 against a vessel wall, a dilation balloon, such as an angioplasty dilation balloon as described above, may be directed into pathway 307 of framework 301 through opposing ends 305 and 305', using methods well known in the art. Thereafter, the dilation balloon may be inflated to expand opposing ends 305 and 305' of framework 301, along with the remaining portions of framework 301, including filters 304 and 304', to push the framework 301 against the walls of the vessel and permit establishment of pathway 307 so as to allow substantially full fluid flow through device 300. It should be appreciated that, in an embodiment, only opposing end 305 and 305' may be expanded. When only one opposing end 305 or 305' is expanded, filtration may still occur through the other opposing end.

In a collapsed position, filters 304 and 304', in an embodiment, may be provided with a diameter sufficient to allow filters 304 and 304' to be positioned within a vessel. Following expansion of the filters 304 and 304', filters 304 and 304' may be provided with a diameter sufficient to be positioned against the wall of the vessel.

In accordance with one embodiment, to provide the expanded portion 302 of framework 301 with an ability to be in an expanded state and form filters 304 and 304' facing one another for capturing clots within the fluid flow, framework 301 may initially be treated and processed by methods known in the art to provide, for example, shape memory ability to the expanded portion 302 of the framework 301, while allowing the filtering arms 303 and 303' and opposing ends 305 and 305' to remain malleable and in a substantially collapsed state. By providing shape memory ability to the expanded portion 302, the expanded portion 302, when inserted into a vessel, can act to pull the malleable filter arms 303 and 303' into a substantially conical configuration to form the filters 304 and 304'. Once shape memory ability has been imparted to the expanded portion 302 of framework 301, where in the natural state the expanded portion 302 is expanded, framework 301 can easily be collapsed and covered by a sheath for delivery to a site of interest. Delivery can be performed by methods known in the art, including the use of a catheter. Upon arrival at the site of interest, the sheath may be removed to allow the shaped memory expanded portion 302 to expand to its natural state to form filters 304 and 304', so as to secure the framework 301 against the wall of the vessel.

Referring now to FIG. 4B, the filter device can have only one filter 304, with expanded portion 302 positioned at one end of the framework for secured placement of the filter device against the vessel wall. The filter 304, in one embodiment, may be defined by a plurality of arms 303 terminating at malleable portion 305. Arms 303 can act to catch undesirable materials, such as clots, as they flow by. In another embodiment, a lengthened expanded portion 302', as shown in FIG. 4C, can be provided so as to increase or strengthen the secured placement of the filter device against the vessel wall. The lengthened expanded portion 302' can minimize filter tilting when placed in the vessel. In an example, lengthened expanded portion 302' is substantially elongated so as to be longer than the filter arms 303 and the malleable portion 305. The filter arms 303 can be spring hardened and thus self-expanding. Alternatively, the filter arms 303 can be processed to be malleable so as to decrease their stiffness, such that upon implantation, the filter arms 303 can stay in a substantially collapsed position in a neutral state without significant expansion. That is, the filter arms 303 can extend radially inward from the expanded portion 302 to the malleable portion 305 in the neutral state, until the malleable portion 305 is dilated to deploy the filter arms 303 and to reestablish a substantially tubular pathway from the expanded portion 302 to the malleable portion 305.

It should be appreciated that although described above as being formed from both substantially malleable materials and shape memory materials, framework 301 can, if desired, be formed entirely from shape memory materials or entirely from substantially malleable materials. Of course, framework 301 can, if desired, be formed from any other materials that are commercially available.

Turning to FIGS. 5A-5C, there is illustrated an anti-tilt filter device 400 in accordance with one embodiment of the present invention. Device 400 can include support 402 and filter 403, formed by arms 408 and arms 408', respectively. Arms 408, in an embodiment, may provide desired stability or support to device 400, as well as a self-centering capability. This way, when device 400 is delivered and deployed in a vessel, arms 408 may prevent device 400 from tilting by pressing against the vessel wall, while allowing device 400 and, in particular, filter 403, to be centered. To that end, arms 408 may be made from materials having sufficient stiffness and/or inflexibility for support. Arms 408 may also have sufficient self-expanding properties.

Arms 408', in an embodiment, can act to capture undesirable materials flowing through the vessel. It should be noted that device 400 can be placed in either direction in the vessel. In certain embodiments, when device 400 is so placed such that flow direction is from arms 408 to arms 408', arms 408 and 408' can be so configured that undesirable materials can pass through arms 408 and be captured on arms 408' without passing therethrough. For example, the space between arms 408 can be sufficiently large while the space between arms 408' being sufficiently small. In an embodiment, there can be more arms 408' than arms 408, such that there is less space between arms 408' than arms 408. Furthermore, when flow direction is from arms 408 to arms 408', arms 408' can also act to direct undesirable materials captured thereon to move along the arms 408', away from the center of the vessel and toward the periphery of the vessel. Alternatively, when device 400 is so placed such that flow direction is from arms 408' to arms 408, undesirable materials can be captured by arms 408' and directed therealong toward the center of the vessel.

Arms 408 and 408' can be connected by a central portion 404, which in its neutral state can be in a substantially collapsed position, as shown in FIG. 5A. Central portion 404, in some embodiments, does not require external force to keep it in the collapsed position; that is, arms 408 and 408' while being connected to central portion 404, do not act to apply a force to push or hold the central portion 404 in the collapsed position. In an embodiment, when the filter 403 is no longer needed, central portion 404 can be dilated to eliminate filter 403 and to reestablish a pathway extending through the device 400.

To make the device 400, a patterned frame having, for example, four portions, end 401, central portion 404, arms 408, and arms 408', as shown in FIG. 5B, can be used. The frame can be a nitinol frame laser cut from a thin-walled nitinol tube. Any other materials (e.g., elastic or superelastic) discussed herein can also be used to pattern, construct or form the frame. In an embodiment, the frame can be formed in a way such that there are more arms 408' than arms 408. The arms 408 and arms 408' can also have different profiles (e.g., arms 408 may have a smaller cross-sectional profile than that of arms 408').

End 401, in an embodiment, can be designed and processed, using materials and methods discussed herein, to have self-expanding properties so as to provide secured placement of the device 400 against a vessel wall, when device 400 is in the filter mode (FIG. 5B). Central portion 404 can also be designed and processed, using materials and methods discussed herein, to be substantially constricted or collapsed in its neutral state, as shown in FIG. 5B.

In its filter mode, as shown in FIG. 5C, arms 408 and arms 408' may expand out to substantially the same diameter, so that both ends can securely press against the wall of vessel 105 to ensure deployment without tilting of the filter. To that end, materials at both ends of the device 400 can be processed to have self-expanding properties so as to provide secured placement of the device, at both ends, against the wall of vessel 105. In an embodiment, clot 110 that passes through the arms 408 can be captured by arms 408' and be directed therealong away from the center of the vessel toward the wall of vessel 105, as the arms 408' radiate outwardly toward the wall of vessel 105. As such, clot 110' can be caught near the wall of vessel 105 (i.e., in the periphery).

With such asymmetrical device 400, an increased passage of clots passing through the arms 408 may be achieved, as arms 408 may be designed to be sufficiently spaced from each other to allow passage of clots. This design may lead to greater clot capture by the distal arms 408', where the clots may be captured in the periphery of the vessel. As discussed above, by capturing clots in the periphery of the vessel, the higher velocity flow in the center of the vessel may be preserved, thereby providing less disruption to venous flow in the patient.

In operation, to prepare the vascular filter device for insertion in the body, a user can initially collapse the vascular filter device for insertion into a delivery mechanism, for example, a catheter. Once loaded into a delivery mechanism, the delivery mechanism may be inserted into the body, and advanced along a vessel within the body (e.g. the inferior vena cava) to a site of interest for implantation. The filter device may then be removed from within the delivery mechanism and permitted to expand. The expansion of the device or framework allows the device to engage the wall of the vessel, as shown in FIGS. 1-5, and to minimize subsequent movement of the device from the site of implantation. When engaging the vessel wall, securing mechanisms on the framework of the device can secure the framework against the vessel wall. Upon expansion of the device or framework, at least one filter having a substantially conical shape may be formed. With the vascular filter device deployed and engaged within the vessel, blood clots and other debris can subsequently be captured within the filter or filters.

In various embodiments, the filter device can be bi-directional such that the device may be placed in a vessel in either direction to capture clots. In this way, the need associated with uni-directional filters to place them in a particular direction (e.g., along the blood flow) is eliminated.

The bi-directional filter device, in some embodiments, can include two sets of opposing arms that are positioned in a way so as to each define a filter. Furthermore, the two sets of arms can be offset, to the extent desired, from one another, as opposed to be in a substantially aligned relation. In that way, while the first set of arms can act to capture undesirable materials (e.g., stringy clots), those that may have bypassed the first set of arms (e.g., passing through the spaces between two adjacent arms) can be captured by the second set of arms that are offset from the first set. Therefore, this design maximizes clots capturing.

Once the filtering function is no longer necessary, it may be desirable to reverse (i.e., eliminate) the filter or filters and reestablish the pathway through the device. Reversal of the filtering function may involve elimination of the filters manually. Manual removal may include, for example, advancing into the vena cava a device capable of severing the filter or filter formation element, locating the filter or filter formation element, and severing the filter or filter formation element. Severing the filter or filter formation element may involve cutting the wires or the mechanism holding the filter in place. In another embodiment, the filter or filter formation element can be removed by permitting their resorption or degradation over a period of time.

A method of manufacturing a filter in accordance with the present invention is also provided. In some embodiments, metals, including superelastic metals, may have a hardened state. In a hardened state, the metal may be made to be self-expanding and spring-like. In other embodiments, metals, including superelastic metals, may have an annealed state. In an annealed state, the metal may be made to be deformable and malleable. A filter framework, in accordance with one embodiment, may be manufactured from a single tube. The single tube may, in an embodiment, be in an annealed state, where it is soft and malleable. The tube, for example, can then be cut using laser or other methods known in the art to yield the desired framework. Once the desired framework is produced, the malleable framework can, in an embodiment, be expanded mechanically using, for instance, a dilation balloon or other dilation device to form a filter or "butterfly" configuration, as illustrated, for instance, in FIGS. 1A and 2A. Once expanded, the tube may remain in the "butterfly" configuration. While in this configuration, the framework may, in one embodiment, be treated and processed by first heating the framework to a substantially high temperature and then quenching the framework in a low temperature fluid bath to harden the entire filter and produce spring-like properties. It should be appreciated that other methods known in the art may also be used to provide spring-like properties to the framework.

In some embodiments, it may be desired that certain portions, such as the filter arms and/or the middle portion, of the framework be malleable. Where malleability is desired, portions of the framework may be treated and processed by first heating the desired portions, and then letting the desired portions cool at a substantially slower rate, for instance, in the air. In one embodiment, the filter arms and the middle portion may be made malleable by reheating and allowing room cooling of these areas. The process of heating followed by air cooling is able to anneal and soften the filter arms and the middle portion making them malleable. Of course, other methods known in the art can also be used to treat and process the framework so as to provide malleable characteristics to the desired portions.

It should be appreciated, that although described as being formed from a single tube, the filter may be formed from multiple components that can be joined together to form a framework.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A filter device comprising:
   a single-piece filter made from one material, the filter having multiple portions, each portion being separately processed to have different characteristics of self-expansion or malleability;
   a first self-expanding framework portion for secured placement of the device against a wall of a vessel in the presence of fluid flow within the vessel;
   a malleable portion in spaced relation from the first self-expanding framework portion, the malleable portion having a passage therethrough and designed to remain in a neutral, substantially collapsed state with a constricted diameter that is expandable by a dilation balloon, the substantially collapsed state being maintained independent of external forces until the malleable portion is dilated to an expanded state with a diameter substantially similar to that of the first self-expanding framework portion; and
   a plurality of arms extending from the first self-expanding framework portion to the malleable portion and being integral therewith, the plurality of arms being spaced from one another so that when the arms are in an expanded state the malleable portion remains in the constricted diameter independent of external forces, and the arms can act to direct undesirable materials captured thereon from within the fluid flow along a predefined path while allowing the fluid flow to pass through the space between adjacent arms to maintain its flow direction through the device, the plurality of arms being in physical contact with the malleable portion but not exerting any substantial force on the malleable portion to keep it in the substantially collapsed state.

2. The filter device of claim 1, wherein the first self-expanding framework portion includes an attachment mechanism to enhance secured placement of the device against the wall of the vessel.

3. The filter device of claim 1, wherein the malleable portion, upon dilation, establishes a substantially tubular pathway extending from the first self-expanding framework portion to the malleable portion.

4. The filter device of claim 1, wherein the plurality of arms extend radially inward from the first self-expanding framework portion to the malleable portion.

5. The filter device of claim 1, wherein the plurality of arms are malleable.

6. The filter device of claim 1, wherein the predefined path is between the first self-expanding framework portion and the malleable portion.

7. The filter device of claim 1 further comprising an opposing self-expanding framework portion in axial alignment with the first self-expanding framework portion, such that the malleable portion is situated between the first self-expanding framework portion and the opposing self-expanding framework portion.

8. The filter device of claim 7 further comprising a second set of plurality of arms extending from the opposing self-expanding framework portion and terminating at the malleable portion, the second set of plurality of arms being in physical contact with the malleable portion but not exerting any substantial force on the malleable portion to keep it in the substantially collapsed state.

9. The filter device of claim 8, wherein the second set of plurality of arms between the opposing self-expanding framework portion and the malleable portion are offset from the plurality of arms between the first self-expanding framework portion and the malleable portion, so as to capture undesirable materials that bypass the plurality of arms between the first self-expanding framework portion and the malleable portion.

10. The filter device of claim 1 further comprising a second self-expanding framework portion adjacent to the first self-expanding framework portion and in axial alignment therewith.

11. The filter device of claim 10 further comprising:
a second malleable portion in spaced relation from the second self-expanding framework portion and designed to remain in a neutral, substantially collapsed state with a constricted diameter that is expandable by a dilation balloon, the substantially collapsed state being maintained independent of external forces until the second malleable portion is dilated to an expanded state with a diameter substantially similar to that of the first self-expanding framework portion; and
a second set of plurality of arms extending from the second self-expanding framework portion and terminating at the second malleable portion, the second set of plurality of arms being in physical contact with the second malleable portion but not exerting any substantial force on the second malleable portion to keep it in the substantially collapsed state.

12. The filter device of claim 11, wherein the second set of plurality of arms between the second self-expanding framework portion and the second malleable portion are offset from the plurality of arms between the first self-expanding framework portion and the malleable portion, so as to capture undesirable materials that bypass the plurality of arms between the first self-expanding framework portion and the malleable portion.

13. The filter device of claim 10, wherein the second self-expanding framework portion and the first self-expanding framework portion are integral to provide substantially one framework for secured placement of the device against the wall of the vessel.

14. The filter device of claim 1, wherein the device is made of a biocompatible material.

15. A method for capturing undesirable materials, comprising:
securing, against a wall of a vessel, a single-piece filter made from one material, the filter having multiple portions, each portion being separately processed so have different characteristics of self-expansion or malleability, the filter having a first self-expanding framework portion having a plurality of arms extending from the framework and radially inward to terminate at a substantially collapsed malleable portion having a passage therethrough, the plurality of arms being integral with and in physical contact with the malleable portion but not exerting any substantial force on the malleable portion to keep it in the substantially collapsed state, the malleable portion having a constricted diameter that is expandable by a dilation balloon;
permitting the malleable portion to remain substantially collapsed independent of external forces;
allowing undesirable materials within a fluid flow to flow into the framework toward the arms to permit the undesirable material to be captured thereon while allowing the fluid flow to pass through the space between adjacent arms to maintain its flow direction through the vessel; and
directing the captured undesirable materials on the arms along a predefined path between the first self-expanding framework and the malleable portion.

16. The method of claim 15 further comprising dilating the substantially collapsed malleable portion to establish a substantially tubular pathway extending from the first self-expanding framework portion to the malleable portion to minimize any interference with fluid flow through the framework.

17. The method of claim 15 further comprising securing, against the wall of the vessel, an opposing self-expanding framework portion having a plurality of arms extending from the opposing framework and radially inward to terminate at the substantially collapsed malleable portion, such that the malleable portion is situated between the first self-expanding framework portion and the opposing self-expanding framework portion.

18. The method of claim 17, wherein the step of securing includes off-setting the plurality of arms between the opposing self-expanding framework portion and the malleable portion from the plurality of arms between the first self-expanding framework portion and the malleable portion.

19. The method of claim 18, further including permitting undesirable materials passing through the set of arms between the first framework portion and the malleable portion to be captured by the off-set set of arms between the opposing framework portion and the malleable portion.

20. The method of claim 19, further including directing the undesirable materials captured on the off-set set of arms between the opposing framework portion and the malleable portion along a defined pathway on the arms away from the malleable portion.

21. The method of claim 19, wherein the second self-expanding framework portion and the first self-expanding framework portion are integral to provide substantially one framework for secured placement of the device against the wall of the vessel.

22. The method of claim 15 further comprising attaching, against the wall of the vessel, a second self-expanding framework portion adjacent to the first self-expanding framework portion and in axial alignment therewith, the second framework portion having plurality of arms extending from the second framework and radially inward to terminate at a second substantially collapsed malleable portion.

23. The method of claim 22, wherein the step of attaching includes off-setting the set of arms between the second self-expanding framework portion and the second malleable portion from the set of arms between the first self-expanding framework portion and the malleable portion.

24. The method of claim 22, further including permitting undesirable materials passing through the set of arms between the first framework portion and the malleable portion to be captured by the off-set set of arms between the second framework portion and second malleable portion.

* * * * *